United States Patent
Rane et al.

(10) Patent No.: US 12,412,125 B2
(45) Date of Patent: Sep. 9, 2025

(54) VIRTUAL NOSE USING QUANTUM MACHINE LEARNING AND QUANTUM SIMULATION

(71) Applicant: Accenture Global Solutions Limited, Dublin (IE)

(72) Inventors: Parag Rane, Thane (IN); Payal Agarwal, Mumbai (IN); Prasanna Srinivasa Rao, Bengaluru (IN); Gopali Raval Contractor, Mumbai (IN); Adnan Khan, Gurgaon (IN); Mukesh Kumar Chaudhary, Bangalore (IN); Saurabh Juneja, New Delhi (IN)

(73) Assignee: Accenture Global Solutions Limited, Dublin (IE)

( * ) Notice: Subject to any disclaimer, the term of this patent is extended or adjusted under 35 U.S.C. 154(b) by 891 days.

(21) Appl. No.: 17/649,852

(22) Filed: Feb. 3, 2022

(65) Prior Publication Data
US 2023/0244988 A1    Aug. 3, 2023

(51) Int. Cl.
*G06N 20/00* (2019.01)
*G06N 10/80* (2022.01)

(52) U.S. Cl.
CPC ............. *G06N 20/00* (2019.01); *G06N 10/80* (2022.01)

(58) Field of Classification Search
CPC ........ G06N 20/00; G06N 10/80; G06N 10/20; G06N 10/60; G06N 3/0455; G01N 33/004
See application file for complete search history.

(56) References Cited

U.S. PATENT DOCUMENTS

| | | | |
|---|---|---|---|
| 11,055,356 B2 | 7/2021 | Ritchey et al. | |
| 2018/0260686 A1* | 9/2018 | Tommy | G01N 33/0001 |
| 2018/0260731 A1* | 9/2018 | Zeng | G06N 10/60 |
| 2020/0169396 A1* | 5/2020 | Neven | G06N 3/063 |
| 2020/0272930 A1* | 8/2020 | Aspuru-Guzik | G06N 3/082 |
| 2020/0300829 A1* | 9/2020 | Sobel | G01N 33/0036 |
| 2020/0358187 A1 | 11/2020 | Tran et al. | |
| 2021/0199627 A1 | 7/2021 | Steen et al. | |
| 2022/0076131 A1* | 3/2022 | Rolfe | G06N 3/086 |

(Continued)

OTHER PUBLICATIONS

Reddy, "A hybrid quantum regression model for the prediction of molecular atomization energies", Mach. Learn.: Sci. Technol. 2 (2021) 025019. (Year: 2021).*

(Continued)

*Primary Examiner* — Dave Misir
(74) *Attorney, Agent, or Firm* — POLSINELLI PC

(57) ABSTRACT

In some implementations, an olfaction system may receive partition coefficients associated with one or more molecules detected in a headspace of a sample captured from an environment. The olfaction system may generate a quantum-ready dataset based on the partition coefficients using a partial quantum autoencoder that includes one or more quantum gate layers. The olfaction system may use a quantum approximate optimization algorithm to identify, within a spectrum of potential smells simulated by a quantum circuit, a set of smells emitted by the sample based on the quantum-ready dataset. The olfaction system may map a set of objects to the set of smells emitted by the sample. The olfaction system may predict a future state associated with the set of smells emitted by the sample using one or more hybrid quantum machine learning models.

20 Claims, 8 Drawing Sheets

(56) References Cited

U.S. PATENT DOCUMENTS

2022/0383992 A1* 12/2022 Triendl ................. G06N 3/045
2024/0021275 A1* 1/2024 Wiltschko ............. G06N 3/096

OTHER PUBLICATIONS

Covington J.A., et al., "Artificial Olfaction in the 21st Century," IEEE Sensors Journal, Jun. 2021, vol. 21(11), pp. 12969-12990.
Extended European Search Report for Application No. EP22193072, mailed on Jul. 12, 2023, 12 pages.
Guo J., et al., "ODRP: A Deep Learning Framework for Odor Descriptor Rating Prediction Using Electronic Nose," IEEE Sensors Journal, IEEE, Jul. 2021, vol. 21(13), pp. 15012-15021.
IBM Research Editorial Staff, "Using AI to Create New Fragrances," IBM Research Blog, Oct. 23, 2018, 8 pages. [Retrieved from https://www.ibm.com/blogs/research/2018/10/ai-fragrances/].
Botha, "Computer develops fragrances for the perfume industry," Medium, Jan. 16, 2019, 3 pages. (Retrieved from https://medium.com/the-future-world/computer-develops-fragrances-for-the-perfume-industry-c83ed0c6782].

\* cited by examiner

VIRTUAL NOSE USING QUANTUM MACHINE LEARNING AND QUANTUM SIMULATION

BACKGROUND

The sense of smell, or olfaction, is a special sense (e.g., a sense with a specialized and devoted organ, in this case the nose) through which smells (or odors) are perceived. The sense of smell has many functions, including detecting hazards (e.g., leaking gas or spoiled food) and pheromones, and also plays a role in taste. In humans and other vertebrates, olfaction generally occurs when one or more volatilized molecules or chemical compounds emitting an odor (without positive or negative connotations) bind to receptors within the nasal cavity, causing signals to be transmitted through the olfactory system. Glomeruli, which are spherical structures located in the olfactory bulb of the brain, aggregate the signals from the receptors and transmit the signals to the olfactory bulb, where the sensory input interacts with parts of the brain responsible for smell identification, memory, emotion, and/or taste, among other examples.

SUMMARY

Some implementations described herein relate to a method. The method may include receiving, by a device, an input dataset that includes partition coefficients associated with one or more molecules detected in a headspace of a sample captured from an environment. The method may include generating, by the device, a quantum-ready dataset based on the partition coefficients using a partial quantum autoencoder that includes one or more quantum gate layers, where an input to the partial quantum autoencoder includes the partition coefficients and a number of quantum bits to use in the one or more quantum gate layers. The method may include using, by the device, a quantum approximate optimization algorithm to identify, within a spectrum of potential smells simulated by a quantum circuit, a set of smells emitted by the sample based on the quantum-ready dataset. The method may include mapping, by the device, a set of objects to the set of smells emitted by the sample. The method may include predicting, by the device, a future state associated with the set of smells emitted by the sample using one or more hybrid quantum machine learning models. The method may include providing, by the device, an output that indicates the set of objects mapped to the set of smells emitted by the sample and indicates the future state associated with the set of smells.

Some implementations described herein relate to a device. The device may include one or more memories and one or more processors coupled to the one or more memories. The one or more processors may be configured to receive an input dataset that includes partition coefficients associated with one or more molecules detected in a headspace of a sample captured from an environment. The one or more processors may be configured to generate a quantum-ready dataset based on the partition coefficients using a partial quantum autoencoder that includes one or more quantum gate layers. The one or more processors may be configured to use a quantum approximate optimization algorithm to identify, within a spectrum of potential smells simulated by a quantum circuit, a set of smells emitted by the sample based on the quantum-ready dataset. The one or more processors may be configured to map a set of objects to the set of smells emitted by the sample. The one or more processors may be configured to provide an output that indicates the set of objects mapped to the set of smells emitted by the sample. The one or more processors may be configured to provide, to a sampling system, feedback to control a size of a next sample captured from the environment in a next olfaction iteration based on a quantity of objects in the set of objects mapped to the set of smells emitted by the sample.

Some implementations described herein relate to a non-transitory computer-readable medium that stores a set of instructions for a device. The set of instructions, when executed by one or more processors of the device, may cause the device to receive an input dataset that includes partition coefficients associated with one or more molecules detected in a headspace of a sample captured from an environment. The set of instructions, when executed by one or more processors of the device, may cause the device to generate a quantum-ready dataset based on the partition coefficients. The set of instructions, when executed by one or more processors of the device, may cause the device to use a quantum approximate optimization algorithm to identify, within a spectrum of potential smells simulated by a quantum circuit, a set of smells emitted by the sample based on the quantum-ready dataset. The set of instructions, when executed by one or more processors of the device, may cause the device to perform spectrum matching to map the set of smells to a set of objects. The set of instructions, when executed by one or more processors of the device, may cause the device to predict a future state associated with the set of smells emitted by the sample using one or more machine learning models. The set of instructions, when executed by one or more processors of the device, may cause the device to provide an output that indicates the set of objects mapped to the set of smells emitted by the sample and indicates the future state associated with the set of smells.

DETAILED DESCRIPTION

Figure 1A:
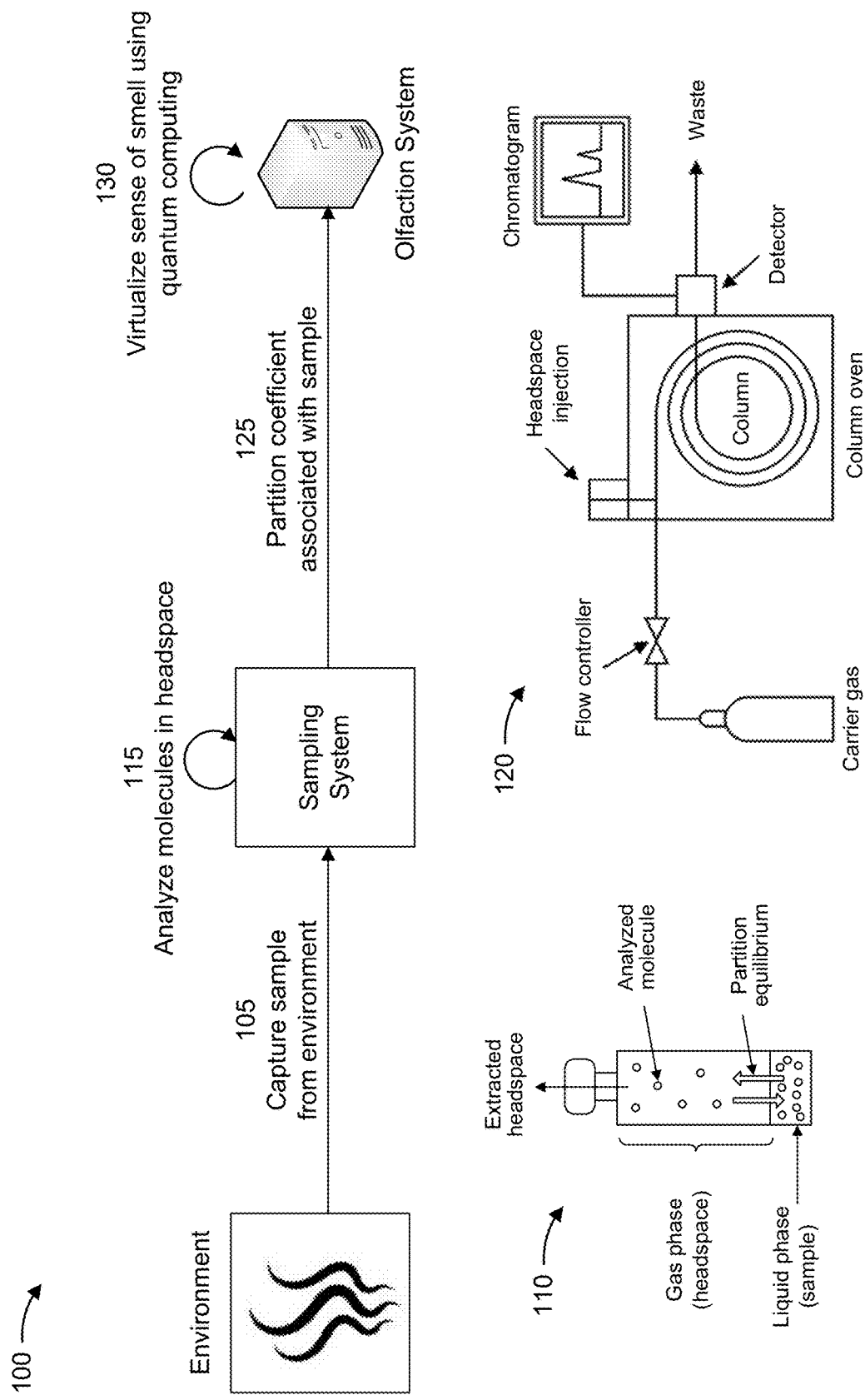
FIGS. 1A-1D are diagrams of an example implementation associated with a virtual nose using quantum machine learning and quantum simulation, as described herein.

The following detailed description of example implementations refers to the accompanying drawings. The same reference numbers in different drawings may identify the same or similar elements.

Machine perception refers to technologies that simulate the ways that humans (or potentially other vertebrates or organisms) use senses and sensory organs to perceive the surrounding world. In particular, machine perception technologies typically use attached hardware to obtain sensory input data, which may then be interpreted in a manner that is similar to (or simulates) the way that humans use senses to see, hear, touch, smell, and/or taste. For example, computer vision technologies may acquire, process, analyze, and understand image data (e.g., obtained using cameras or scanners) to virtualize the sense of sight, machine hearing (or audition) technologies may gather and process sound data (e.g., obtained using microphones) to virtualize the sense of hearing and enable applications such as speech analytics (e.g., speech recognition and/or speech synthesis), and machine touch technologies may gather and process tactile input data (e.g., obtained using one or more sensors) to virtualize the sense of touch. However, virtualizing the sense of smell (and the related sense of taste) is notoriously challenging, and available technologies that are designed to virtualize olfaction suffer from drawbacks.

For example, one existing technique designed to virtualize the sense of smell is to sense and classify airborne chemicals using an electronic sensor, sometimes referred to as an electronic nose. In particular, electronic noses typically include a sample delivery system, a detection system, and a computing system, where the sample delivery system injects a headspace gas obtained from a sample into the detection system, which uses a chemical sensor array, mass spectrometry, and/or gas chromatography to detect the volatile compounds in the headspace gas. The computing unit then uses correlation and/or pattern recognition techniques to generate signal patterns that are used to characterize smells or odors emitted by the sample. Accordingly, the techniques used in existing electronic noses or other machine olfaction systems can be used to identify thousands of unique smells or odors. However, current research suggests that the average human can distinguish more than one trillion unique smells, which far exceeds the capabilities of the highest performing electronic noses. Furthermore, existing machine olfaction systems lack capabilities to predict the future state of a smell or odor (e.g., how the smell or odor may disperse over time, how long the smell or odor will last, and/or how strong the smell or odor will be at a future point in time). Accordingly, existing machine olfaction systems suffer from drawbacks that include poor accuracy and a limited range of detectable smells, an inability to predict the future state of a smell, and the use of computationally intensive and time-consuming correlation and/or pattern recognition techniques, among other examples.

Some implementations described herein may use quantum computing techniques to virtualize the sense of smell (e.g., perform machine olfaction). More particularly, as described in further detail herein, some implementations may use techniques such as quantum simulation and hybrid quantum machine learning to simulate a spectrum of smells, predict the future state of a smell, and/or generate feedback to improve accuracy of the machine olfaction over time. For example, in some implementations, an olfaction system may receive a set of partition coefficients that represent ratios of concentrations of one or more molecules or compounds in a sample, which may be passed through a partial quantum autoencoder that generates a quantum-ready dataset based on the set of partition coefficients. The quantum-ready data may then be input to a quantum circuit that simulates molecular properties associated with the spectrum of smells (e.g., molecular compositions, vibrations, and/or non-covalent bonds) and uses a quantum approximate optimization algorithm (QAOA) to generate a set of potential smells emitted by one or more objects contained in the sample. In some implementations, the olfaction system may use a spectrum matching technique to map the set of potential smells to a set of objects, and the olfaction system may generate a quantum graph that includes a number of vertices (or nodes) corresponding to a number of objects mapped to the set of potential smells. In some implementations, the olfaction system may use one or more quantum hybrid machine learning models to predict a future state of the smells, such as a dispersion of the smells, a duration of the smells, and/or a strength of the smells. Furthermore, in some implementations, the olfaction system may provide feedback to the sampling system to control a sample size to capture in a next olfaction iteration (e.g., increasing the sample size, decreasing the sample size, or maintaining the sample size based on the number of objects mapped to the set of potential smells and/or the predicted future state of the smells, among other examples).

In this way, the olfaction system described herein may use quantum computing techniques to significantly increase the range or spectrum of detectable smells and to improve the accuracy and speed of the computations that are performed to enable machine olfaction. Furthermore, the partial quantum autoencoder may provide a capability to convert classical data (e.g., a set of partition coefficients) into quantum-ready data, whereby the olfaction system may be integrated or otherwise backwards-compatible with sample delivery and/or detection systems used in existing electronic noses (e.g., leveraging quantum computing to replace the correlation and/or pattern recognition techniques used in existing electronic noses). Furthermore, the olfaction system uses quantum feedback to improve the accuracy of the sample delivery and detection subsystem(s) through continuous learning, and uses quantum hybrid machine learning to predict a future state and/or effect of one or more smells. In this way, the olfaction system described herein may offer significantly improved performance over existing electronic noses, which may be applied in various industries (e.g., detecting perishable foods that may have spoiled, increasing human safety by detecting potentially dangerous odors, and/or improving or automating quality control for fast-moving consumer goods such as perfumes or food items).

FIGS. 1A-1D are diagrams of an example implementation 100 associated with a virtual nose using quantum machine learning and quantum simulation, as described herein. As shown in FIGS. 1A-1D, example implementation 100 includes a sampling system and an olfaction system, which are described in more detail below in connection with FIG. 3 and FIG. 4.

As shown in FIG. 1A, and by reference number 105, the sampling system may capture a sample that includes one or more objects that may be emitting or otherwise causing one or more smells within an environment. In some implementations, the sample may generally include a fraction of the surrounding environment in which the olfaction system is performing machine olfaction, where the sample may include molecules or compounds included in solid, liquid, and/or gaseous objects. For example, as shown by reference number 110, the sample captured from the surrounding environment may be placed in a liquid (or sample) phase, which contains molecules or compounds of interest that will diffuse into a gas phase referred to as a headspace until the molecules or compounds in the liquid phase and the gas phase reach equilibrium. Accordingly, the sampling system may be used to generate the headspace that includes molecules (e.g., volatile compounds) that occur within the sample, where the headspace is the analyzed fraction of the surrounding environment. In this way, the sampling system may generate a headspace in substantially constant operating conditions.

As further shown in FIG. 1A, and by reference number 115, the headspace may be extracted (e.g., from a vial or other suitable instrument) by the sampling system, and a detection system may analyze the molecules (e.g., volatile compounds) in the headspace. In some implementations, the detection system may use gas chromatography to separate and analyze substances that are present in the headspace gas, although it will be appreciated that other techniques such as chemical sensor arrays (e.g., reacting to volatile compounds on contact) or mass spectrometry (e.g., measuring a mass-to-charge ratio of molecules in the sample) may be used to detect and/or analyze the molecules that are present in the headspace gas. For example, as described herein, the gas chromatography may be used to separate volatile compounds within the headspace gas, which occurs based on the way in which molecules, compounds, or other substances interact with a mobile phase and a stationary phase in a gas chromatographic column. In particular, in gas chromatography, molecules that are relatively less volatile interact more with the stationary phase and move relatively slowly, and molecules that are more volatile interact more with the mobile phase and move quickly.

For example, in FIG. 1A, reference number 120 illustrates an example gas chromatography system, where the stationary phase is used as a column packed in a glass or metallic tube with an internal diameter that typically ranges from two (2) to ten (10) millimeters and a length from one (1) to twenty (20) meters. As shown, the headspace gas that includes the volatile compounds to be separated is placed on one end of the column using a suitable injection device (e.g., a syringe), and is then driven through the column by an inert or neutral carrier gas (the mobile phase) at a constant speed or rate that is adjustable by a flow controller. The molecules or compounds in the headspace gas are generally separated as the molecules or compounds pass through the column, and the separated fractions gradually emerge at the other end of the column along with the mobile phase. The substances in the emerging mobile phase are then detected or characterized by measuring a physical or chemical property in a detector device (e.g., a fathometer). The measurement may be continuously recorded on a moving chart by a recording device, which results in a gas chromatogram plotting the observed measurements over time. Additionally, or alternatively, the sampling system described herein may use ultra-fast gas chromatography, which uses shorter columns with larger internal diameters to overcome capacity problems and enable faster ramp rates. For example, in ultra-fast gas chromatography, the column may be directly heated in a column compartment without an air-blown column oven, which reduces the amount of mass to be heated such that a ramp rate increases and cool-down occurs more quickly, which may offer faster analysis and thus reduce olfaction response time.

As further shown in FIG. 1A, and by reference number 125, the sampling system may output, to the olfaction system, a set of partition coefficients that represent ratios of concentrations of one or more molecules or compounds that were detected in the headspace gas. For example, when the sampling system detects the molecules or compounds in the headspace gas through ultra-fast gas chromatography or other suitable techniques, the sampling system may provide a peak with respect to a retention time of the sample. Accordingly, based on the output from the ultra-fast gas chromatography or other instrumentation used in the sampling system, the sampling system may create a set of partition coefficients that each represent a respective ratio of a first concentration of a substance (e.g., a molecule or compound) in a first medium or phase (e.g., the mobile phase or the stationary phase) to a second concentration of the substance in a second medium or phase when the two concentrations are at equilibrium.

Accordingly, as further shown in FIG. 1A, and by reference number 130, the olfaction system may virtualize the sense of smell (e.g., perform machine olfaction) using various quantum computing techniques. For example, as described in further detail herein with reference to FIG. 1B, the olfaction system may use a partial quantum autoencoder to generate a quantum-ready dataset based on the set of partition coefficients, and may input the quantum-ready dataset to a quantum circuit that simulates molecular properties associated with the spectrum of smells (e.g., molecular compositions, vibrations, and/or non-covalent bonds). Furthermore, as described in further detail herein with reference to FIG. 1C, the quantum circuit may use a QAOA to generate, based on the quantum-ready dataset, a set of potential smells emitted by one or more objects contained in the sample. As described in further detail herein with reference to FIG. 1D, the olfaction system may then use a spectrum matching technique to map the set of potential smells to a set of objects, and may generate a quantum graph that includes a number of vertices corresponding to a number of objects mapped to the set of potential smells. Accordingly, in some implementations, feedback may be provided to the sampling system to increase, decrease, or maintain a sample size to capture in a next olfaction iteration (e.g., based on a number of nodes in the quantum graph). Furthermore, the olfaction system may use one or more quantum hybrid machine learning models to predict a future state of the detected smells. In some implementations, the feedback used to control the sample size to capture in the next olfaction iteration may be based on the predicted future state of the detected smells.

Figure 1B:
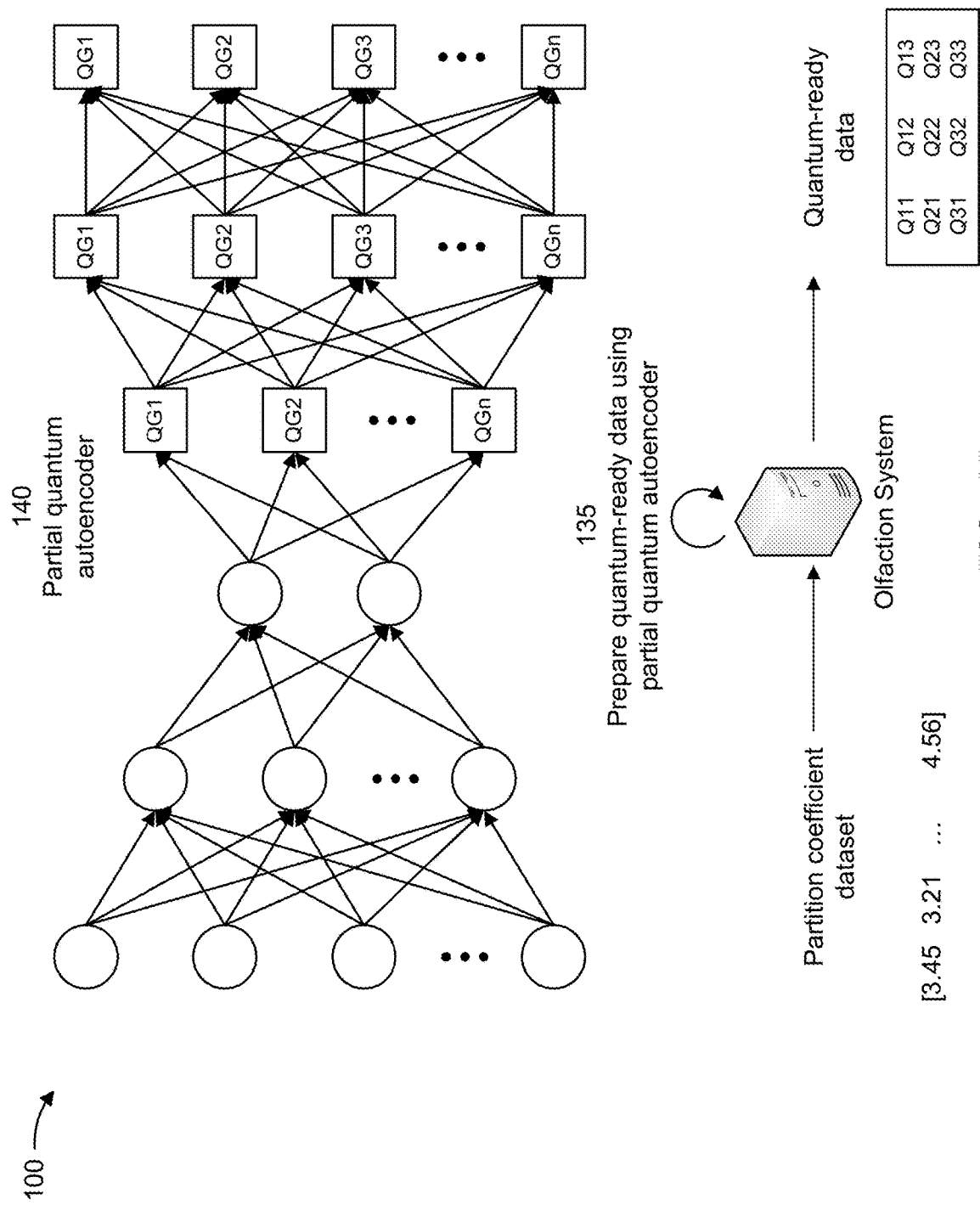

More particularly, as shown in FIG. 1B, and by reference number 135, the olfaction system may prepare the quantum-ready dataset based on the set of partition coefficients using a partial quantum autoencoder. For example, the quantum-ready dataset may have entanglement properties that may improve the prediction of the future state of the smells that are detected in the headspace of the sample, and superposition properties that may increase the range of smells or odors that can be detected based on the partition coefficients. For example, as shown by reference number 140, the partial quantum autoencoder may include a neural network having an input layer (e.g., the leftmost vertical column, where neurons in the input layer are shown as circles) and one or more latent layers (e.g., the second and third vertical columns). In addition, as further shown, the partial quantum autoencoder may include one or more quantum gate layers, shown in vertical columns with squares labelled "QGn" to indicate the respective quantum gates.

In some implementations, an input to the partial quantum autoencoder may include the set of partition coefficients received from the sampling system and a number of quantum bits (or qubits) to be used for the quantum gates. For example, in quantum computing, a qubit is the basic unit of quantum information, which is the quantum version of a binary bit physically realized with a two-state device in classical computing. However, in quantum computing, a qubit is a two-state (or two-level) quantum-mechanical system that exhibits one or more properties of a quantum state. For example, the quantum properties represented by a qubit may include an electron spin in which the two levels can be taken as spin up and spin down, or a photon polarization in which the two states can be taken to be a vertical polarization and a horizontal polarization. Accordingly, whereas a bit has to be in one state or the other (e.g., zero or one) in a classical system, quantum mechanics allows a qubit to be in a coherent superposition of both states simultaneously. In this way, the quantum gate layers may be used to generate a quantum-ready dataset that includes quantum states with a superposition property (e.g., where two or more quantum states can be added together to produce another valid quantum state) and/or an entanglement property (e.g., representing a physical phenomenon that occurs when a group of particles are generated, interact, or share spatial proximity in a way that a quantum state of each particle in the group cannot be described independently of the state of the others). In this way, as described herein, the entanglement property may improve the prediction of the future state of smells detected in the sample and the superposition property may increase the range or spectrum (e.g., quantity) of smells that can be detected in the sample.

For example, in some implementations, after the set of partition coefficients are passed through the neural network input layer and the one or more latent layers, a first quantum gate layer may create a set of quantum states that correspond to a combination of different probabilities that are correlated to different quantum states, where the number of quantum states is generally dependent on the number of qubits used for the quantum gates. In this way, the first quantum gate layer may add a superposition quality or superposition property to the set of partition coefficients, where each quantum gate in the first quantum gate layer may generate a quantum state given by the expression:

$$\text{Quantum state} = \Sigma p\_s|S\rangle$$

where p_s is a probability for a possible measurement in system S and |S> represents the quantum state of system S.

In some implementations, the quantum states output by the first quantum gate layer may be provided to the second quantum gate layer of the partial quantum autoencoder, where the second quantum gate layer may provide a quantum circuit to parameterize the quantum states output by the first quantum gate layer. For example, the quantum circuit may include parameterize circuits to create tunable quantum gates in the second quantum gate layer, which may be represented using the following complex matrix:

$$\begin{bmatrix} \cos a/2 & (\sin a/2) * (-e)^{i\rho} \\ (\sin a/2) * (e)^{i\Omega} & (\cos a/2) * (e)^{i\Omega + i\rho} \end{bmatrix}$$

where a is a quantum state and $\Omega$ and $\rho$ are tunable parameters.

In some implementations, after the quantum states have been parameterized by the second quantum gate layer, a final quantum layer may output the quantum-ready dataset that includes measurements based on the parameterized quantum states output by the second quantum gate layer. For example, the final quantum gate layer may remove one or more quantum states that are associated with a certain class (e.g., molecules or compounds that are associated with a certain class of smells or odors, such as fragrant, fruity, citrus, woody and resinous, chemical, and/or sweet, among other examples) in order to output the quantum-ready dataset that includes the parameterized quantum states to be measured.

Figure 1C:
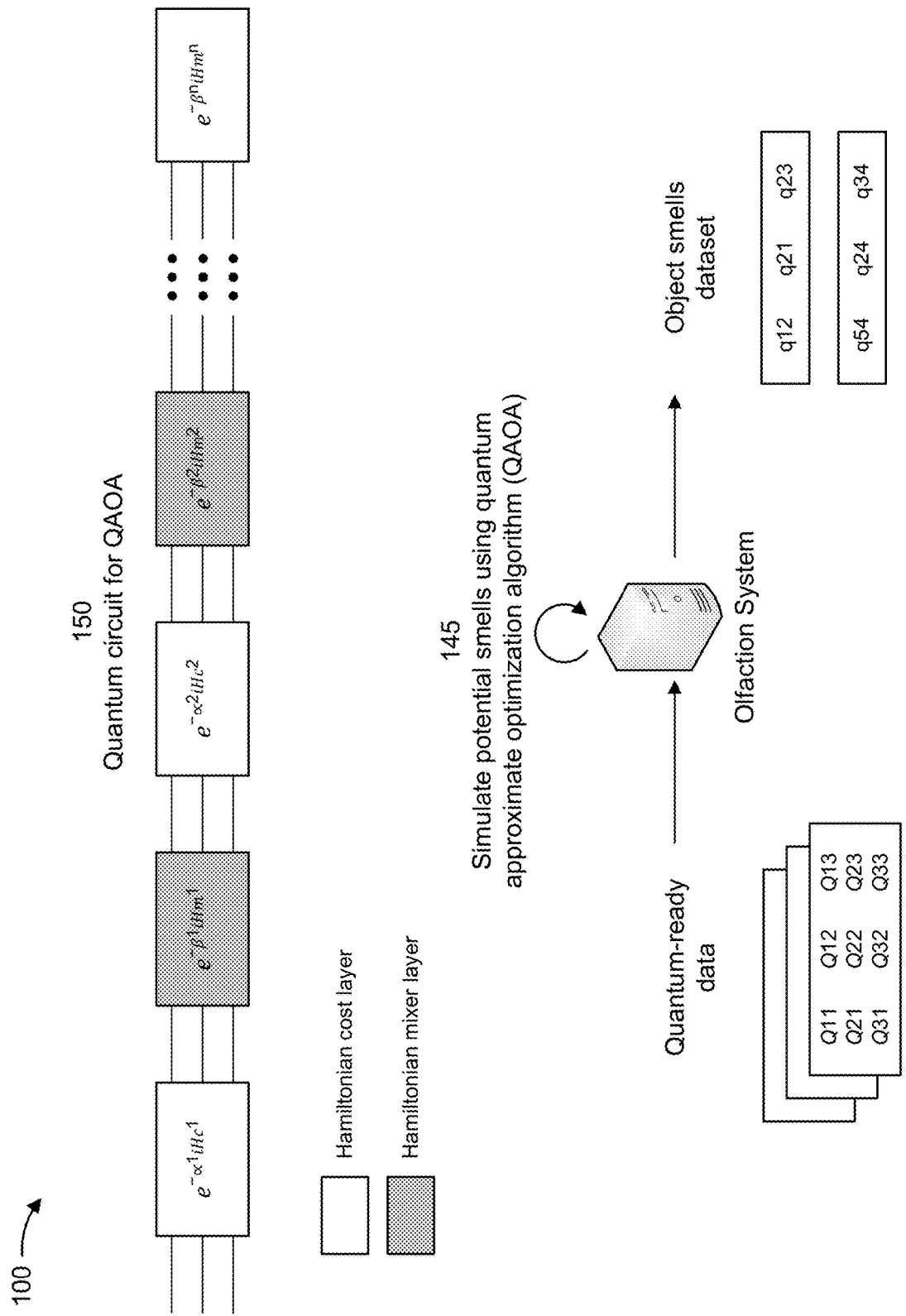

As shown in FIG. 1C, and by reference number 145, the olfaction system may then perform quantum simulation based on the quantum-ready dataset, which may include simulating a spectrum or range of potential smells using a quantum approximate optimization algorithm (QAOA). For example, the QAOA may be used to find approximate solutions to combinatorial optimization problems (e.g., searching for an optimal bitstring), which can be used to optimize and simulate various potential smells based on the quantum-ready dataset that is generated from the set of partition coefficients. For example, as shown by reference number 150, the QAOA may operate in a quantum circuit that simulates molecular properties such as molecular vibrations and non-covalent or other suitable bonds, which can be used to create a spectrum of potential smells that includes many thousands, millions, billions, or more smells. In this way, the quantum circuit used to perform the QAOA may be used to identify an optimal set of one or more object smells (e.g., smells emitted by different objects) from a finite set of object smells.

For example, in order to simulate and identify potential smells in the analyzed headspace of the sample, the olfaction system may define a cost Hamiltonian, $H_c$, such that a ground state of the cost Hamiltonian encodes the solution to the optimization problem, and the olfaction system may further define a mixer Hamiltonian, $H_m$, which is a simple, non-commuting sum of Pauli-x operations. In particular, in quantum mechanics, a Hamiltonian of a system is an operator that corresponds to the total energy of the system, including a sum of the kinetic energies of all particles in the system plus the potential energy of the particles in the system. As shown by reference number 150, the olfaction system may construct the quantum circuit by repeatedly combining alternating Hamiltonian cost layers and Hamiltonian mixer layers in sequence, where a Hamiltonian cost layer is represented as $e^{-\alpha i H_c}$ and a Hamiltonian mixer layer is represented as $e^{-\beta i H_m}$. The olfaction system may initialize $\alpha$ and $\beta$ to optimize the quantum circuit such that measurements output by the quantum circuit after optimization may indicate a set of object smells or odors that were identified based on the quantum-ready dataset. For example, the quantum circuit may generally simulate a spectrum of potential smells based on the way in which different molecules, molecule vibrations, non-covalent bonds, and/or other molecular properties interact to form smells or odors that are emitted by different objects. Accordingly, the output of the quantum circuit may be a set of smells that are potentially emitted by the sample, which may be identified within the spectrum of potential smells simulated by the quantum circuit using the QAOA.

Figure 1D:
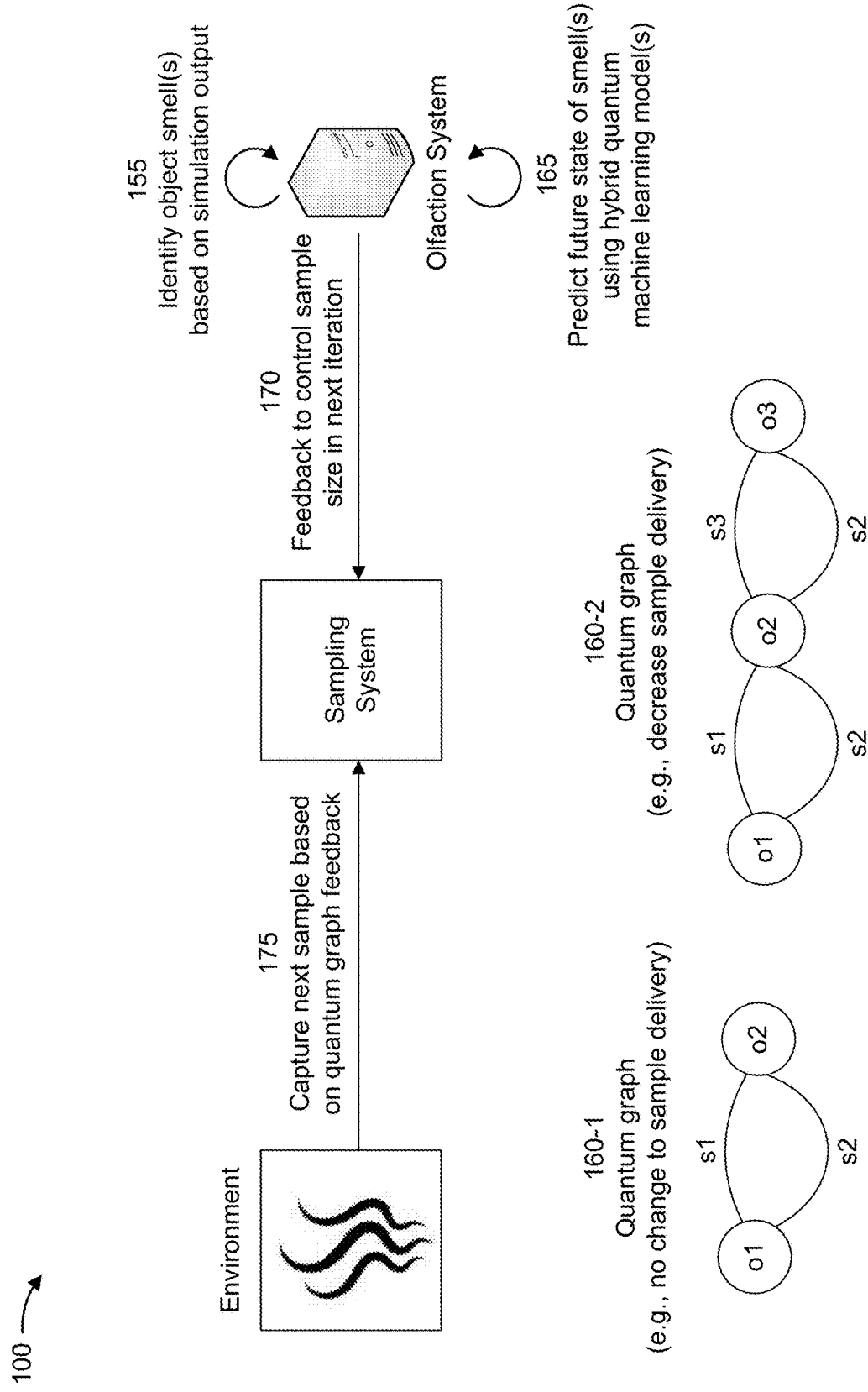

As shown in FIG. 1D, and by reference number 155, the olfaction system may then identify a set of object smells that are mapped to the set of smells based on the output from simulation performed by the quantum circuit. For example, in some implementations, the olfaction system may obtain the set of smells as an output from the quantum circuit that performs the QAOA, and may perform spectrum matching to match the set of smells to a set of objects that may be causing the smell(s). For example, in some implementations, the olfaction system may calculate a distance between each smell included in the simulation output from the quantum circuit shown in FIG. 1C and a spectrum associated with an object, and an object associated with a minimum distance may be identified as causing the smell included in the simulation output from the quantum circuit. In some implementations, as shown by reference number 160-1 and 160-2, the olfaction system may generate a quantum graph to represent the objects and corresponding conditions of the smells emitted by the objects. For example, each quantum state (e.g., bit string) output by the simulation may represent a type of object smell at a current time, where an available vertex or node in the quantum graph may represent an object causing a detected smell and each edge in the quantum graph may represent a condition associated with the object. For example, in FIG. 1D, reference number 160-1 depicts a quantum graph that represents two objects (o1 and o2) with two states (s1 and s2), which may be represented as O1S1O2S2O0. In another example, reference number 160-2 depicts a quantum graph that represents three objects (o1, o2, and o3) with three states (s1, s2, and s3), which may be represented as O1S1O2S2O3S3.

As further shown in FIG. 1D, and by reference number 165, the olfaction system may predict a future state of the set of smells detected using the quantum circuit using one or more hybrid quantum machine learning models. For example, in some implementations, the future state of the one or more smells may relate to a direction in which the smells are moving, dispersion or dilution of the smells within the environment, how fast (or slow) the state of the smells may be changing, a strength or duration of the smells over time, and/or a radius in which the smells will spread, among other examples. In some implementations, the olfaction system may use a quantum regression model to predict the dispersion of the smells within the environment based on parameters such as wind direction, wind speed, humidity, temperature, and the partition coefficients received from the sample delivery system (e.g., based on entanglements represented in the quantum-ready dataset output by the partial quantum autoencoder). Additionally, or alternatively, the olfaction system may use a quantum neural network based on a survival analysis algorithm to identify a strength and/or duration of the smells using the same smell parameters used by the quantum regression model (e.g., wind direction, wind speed, humidity, temperature, and/or partition coefficients).

As further shown in FIG. 1D, and by reference number 170, the olfaction system may provide, to the sampling system, feedback to control a sample size in a next machine olfaction iteration (e.g., based on a quantity of nodes in the quantum graph and/or the predicted future state of the set of smells). For example, the olfaction system may configure a minimum threshold and a maximum threshold or an absolute threshold, which may be used to control (e.g., increase, decrease, or maintain) a size of the next sample that the sampling system captures from the environment. For example, as described above, the quantum graph may generally include a number of nodes or vertices that corresponds to a number of objects that may be causing or emitting the set of smells detected by the quantum circuit, and the size of the next sample captured from the environment may be increased, decreased, or maintained depending on whether the number of vertices in the quantum graph is within a desired range.

For example, as shown by reference number 175, the sample delivery system may increase the size of the next sample captured from the environment (e.g., to increase smell sensitivity) based on the quantity of vertices in the quantum graph failing to satisfy (e.g., failing to equal or exceed) a minimum threshold, decrease the size of the next sample captured from the environment (e.g., to decrease smell sensitivity) based on the quantity of vertices in the quantum graph satisfying (e.g., equaling or exceeding) a maximum threshold (e.g., the sample size may be increased if the quantum graph is null, having no vertices, or may be decreased if the quantum graph includes more than three vertices), or maintain the size of the next sample captured from the environment based on the quantity of vertices in the quantum graph equaling a threshold. For example, in a use case where an objective of the olfaction system is to identify two (2) smells, the threshold may be set to (2), where an ideal situation may be that the number of nodes in the quantum graph satisfies (e.g., equals) the threshold. Accordingly, if two objects with two states can be represented as O1S1O2S2O0, O0O1S1O2S2, OR O1S1O0O2S2, the quantum graph generated to represent the two objects may have the form shown by reference number 160-1. In this case, the quantum graph has two nodes, whereby the feedback provided to the sampling system may indicate that no change to the sample size is needed in the next olfaction iteration. However, if the set of objects mapped to the set of smells is represented as 000000, meaning that no objects were identified, there would be no quantum graph such that the feedback may indicate that the sample size is to be increased in the next olfaction iteration. Alternatively, if the objects and states are represented as O1S1O2S2O3S3, the quantum graph may have the form shown by reference number 160-2, where there are three nodes to represent the three objects. In this case, the number of nodes in the quantum graph fails to satisfy (e.g., exceeds) the threshold, whereby the sample size may be decreased in the next olfaction iteration. Alternatively, if the objects and states mapped to the set of smells are represented as O1S1O000, 000S1O0, or 000O1S1 (one object with one state), the sample size may be increased in the next olfaction iteration based on the number of nodes in the quantum graph failing to satisfy (e.g., being less than) the threshold.

Additionally, or alternatively, in some implementations, the feedback that is used to control the sample size in the next iteration may be based on the predicted future state of the one or more smells. For example, in cases where the predicted future state is determined to be unsatisfactory (e.g., a confidence level fails to satisfy a threshold or the future state is predicted to be a foul or unpleasant odor, among other examples), the feedback may include one or more recommendations and/or automated actions to change the sample to improve the future state (e.g., increase or decrease the sample size to improve the accuracy of the predicted future state and/or change one or more parameters of the sample to improve the odor). In this way, the quantum graph and/or the future state predictions may be used in a continuous feedback loop to control the size or other parameters associated with the samples that are captured in olfaction iterations over time and thereby improve the accuracy and/or granularity of the smell detection performed by the olfaction system.

As indicated above, FIGS. 1A-1D are provided as an example. Other examples may differ from what is described with regard to FIGS. 1A-1D. The number and arrangement of devices shown in FIGS. 1A-1D are provided as an example. In practice, there may be additional devices, fewer devices, different devices, or differently arranged devices than those shown in FIGS. 1A-1D. Furthermore, two or more devices shown in FIGS. 1A-1D may be implemented within a single device, or a single device shown in FIGS. 1A-1D may be implemented as multiple, distributed devices. Additionally, or alternatively, a set of devices (e.g., one or more devices) shown in FIGS. 1A-1D may perform one or more functions described as being performed by another set of devices shown in FIGS. 1A-1D.

Figure 2:
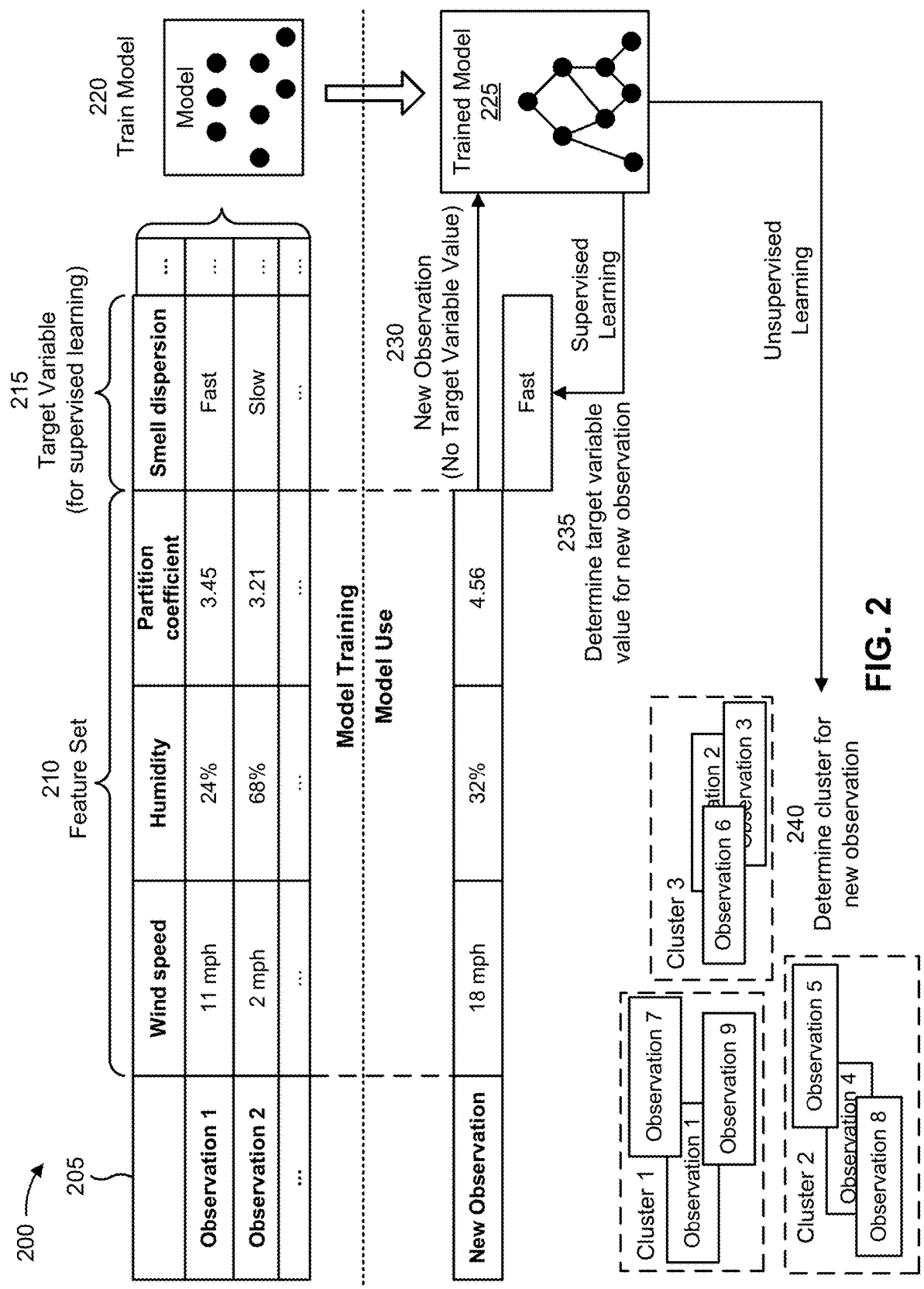
FIG. 2 is a diagram illustrating an example of training and using a machine learning model in connection with enabling machine olfaction using quantum machine learning and quantum simulation, as described herein.

FIG. 2 is a diagram illustrating an example 200 of training and using a machine learning model in connection with virtualizing smell using quantum machine learning and quantum simulation. The machine learning model training and usage described herein may be performed using a machine learning system. The machine learning system may include or may be included in a computing device, a server, a cloud computing environment, or the like, such as the olfaction system described in more detail elsewhere herein.

As shown by reference number 205, a machine learning model may be trained using a set of observations. The set of observations may be obtained from training data (e.g., historical data), such as data gathered during one or more processes described herein. In some implementations, the machine learning system may receive the set of observations (e.g., as input) from the sampling system and/or the olfaction system, as described elsewhere herein.

As shown by reference number 210, the set of observations includes a feature set. The feature set may include a set of variables, and a variable may be referred to as a feature. A specific observation may include a set of variable values (or feature values) corresponding to the set of variables. In some implementations, the machine learning system may determine variables for a set of observations and/or variable values for a specific observation based on input received from the sampling system and/or the olfaction system. For example, the machine learning system may identify a feature set (e.g., one or more features and/or feature values) by extracting the feature set from structured data, by performing natural language processing to extract the feature set from unstructured data, and/or by receiving input from an operator.

As an example, a feature set for a set of observations may include a first feature of wind speed, a second feature of humidity, a third feature of partition coefficient, and so on. As shown, for a first observation, the first feature may have a value of 11 miles per hour (mph), indicating a gentle breeze, the second feature may have a value of 24%, indicating a relatively low humidity, the third feature may have a value of 3.45, indicating a ratio of a concentration of one or more molecules or compounds in a sample, and so on. These features and feature values are provided as examples, and may differ in other examples. For example, the feature set may include one or more of the following features: wind direction, temperature, and/or any other suitable feature that may impact how a smell changes within an environment over time.

As shown by reference number 215, the set of observations may be associated with a target variable. The target variable may represent a variable having a numeric value, may represent a variable having a numeric value that falls within a range of values or has some discrete possible values, may represent a variable that is selectable from one of multiple options (e.g., one of multiples classes, classifications, or labels) and/or may represent a variable having a Boolean value. A target variable may be associated with a target variable value, and a target variable value may be specific to an observation. In example 200, the target variable is smell dispersion, which has a value of fast for the first observation.

The feature set and target variable described above are provided as examples, and other examples may differ from what is described above. For example, for a target variable of smell strength or smell duration, the feature set may include the same features that are used for the target variable of smell dispersion and/or other suitable features.

The target variable may represent a value that a machine learning model is being trained to predict, and the feature set may represent the variables that are input to a trained machine learning model to predict a value for the target variable. The set of observations may include target variable values so that the machine learning model can be trained to recognize patterns in the feature set that lead to a target variable value. A machine learning model that is trained to predict a target variable value may be referred to as a supervised learning model.

In some implementations, the machine learning model may be trained on a set of observations that do not include a target variable. This may be referred to as an unsupervised learning model. In this case, the machine learning model may learn patterns from the set of observations without labeling or supervision, and may provide output that indicates such patterns, such as by using clustering and/or association to identify related groups of items within the set of observations.

As shown by reference number 220, the machine learning system may train a machine learning model using the set of observations and using one or more machine learning algorithms, such as a regression algorithm (e.g., a quantum regression algorithm), a decision tree algorithm, a neural network algorithm (e.g., a quantum neural network with survival analysis), a k-nearest neighbor algorithm, a support vector machine algorithm, or the like. After training, the machine learning system may store the machine learning model as a trained machine learning model 225 to be used to analyze new observations.

As shown by reference number 230, the machine learning system may apply the trained machine learning model 225 to a new observation, such as by receiving a new observation and inputting the new observation to the trained machine learning model 225. As shown, the new observation may include a first feature of an 18 mph wind speed, a second feature of a 32% humidity, a third feature of a 4.56 partition coefficient, and so on, as an example. The machine learning system may apply the trained machine learning model 225 to the new observation to generate an output (e.g., a result). The type of output may depend on the type of machine learning model and/or the type of machine learning task being performed. For example, the output may include a predicted value of a target variable, such as when supervised learning is employed. Additionally, or alternatively, the output may include information that identifies a cluster to which the new observation belongs and/or information that indicates a degree of similarity between the new observation and one or more other observations, such as when unsupervised learning is employed.

As an example, the trained machine learning model 225 may predict a value of fast for the target variable of smell dispersion for the new observation, as shown by reference number 235. Based on this prediction, the machine learning system may provide a first recommendation, may provide output for determination of a first recommendation, may perform a first automated action, and/or may cause a first automated action to be performed (e.g., by instructing another device to perform the automated action), among other examples.

In this way, the machine learning system may apply a rigorous and automated process to predict the future state of one or more smells that are detected by an olfaction system. The machine learning system enables recognition and/or identification of tens, hundreds, thousands, or millions of features and/or feature values for tens, hundreds, thousands, or millions of observations, thereby increasing accuracy and consistency and reducing delay associated with predicting the future state of one or more smells relative to requiring computing resources to be allocated for tens, hundreds, or thousands of operators to manually predict the future state of the one or more smells using the features or feature values.

As indicated above, FIG. 2 is provided as an example. Other examples may differ from what is described in connection with FIG. 2.

Figure 3:
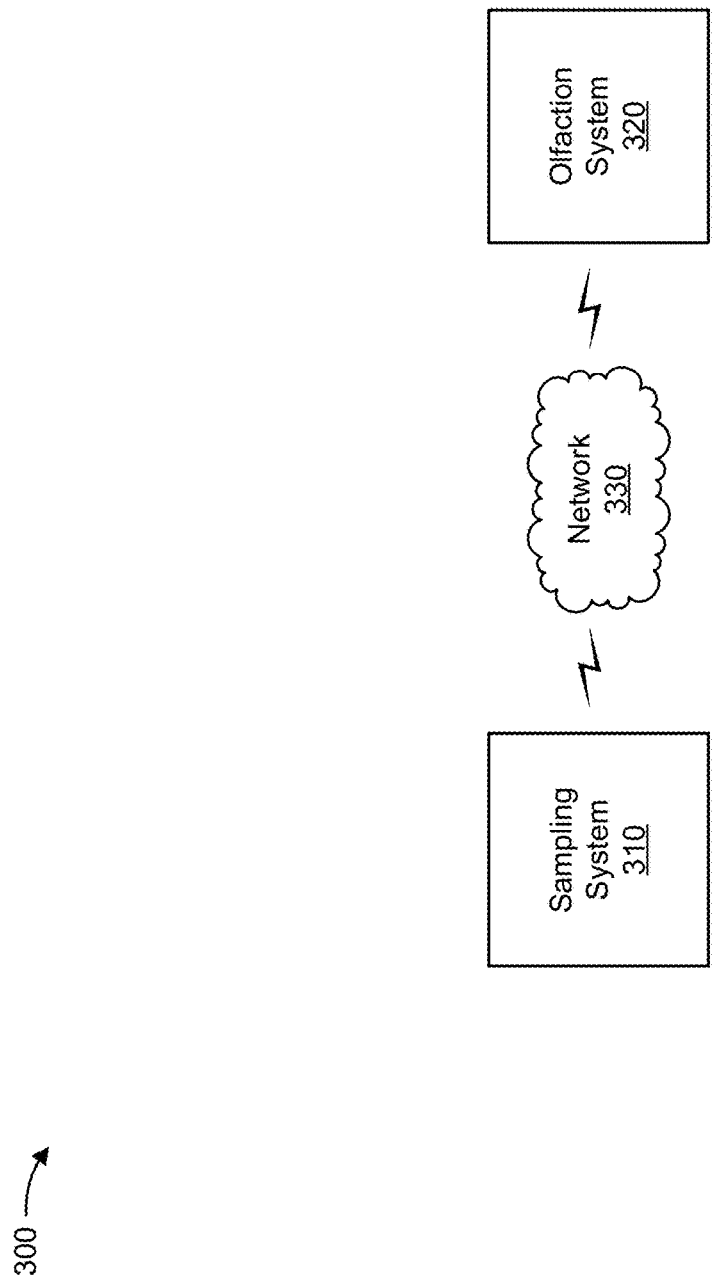
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a sampling system 310, an olfaction system 320, and a network 330. Devices of environment 300 may interconnect via wired connections, wireless connections, or a combination of wired and wireless connections.

The sampling system 310 includes one or more wired or wireless devices capable of receiving, generating, storing, transmitting, processing, detecting, and/or providing information associated with a virtual nose that uses quantum machine learning and quantum simulation to perform machine olfaction, as described elsewhere herein. For example, the sampling system 310 may include a sample delivery system that can capture a sample from an environment and generate a headspace gas to be analyzed, and a detection system that includes one or more sensors that can generate a set of partition coefficients associated with molecules or compounds that are detected in the headspace gas. For example, the detection system may include a gas chromatograph, an ultra-fast gas chromatograph, a mass spectrometer, and/or a chemical sensor array, among other examples. The sampling system 310 may sense or detect a condition or information (e.g., a set of partition coefficients associated with molecules or compounds in a headspace of a sample) and transmit, using a wired or wireless communication interface, an indication of the detected condition or information to other devices in the environment 300.

The olfaction system 320 includes one or more devices capable of receiving, generating, storing, processing, and/or providing information associated with a virtual nose that uses quantum machine learning and quantum simulation to perform machine olfaction. For example, as described elsewhere herein, the olfaction system 320 may use a partial quantum autoencoder to generate a quantum-ready dataset based on a set of partition coefficients received from the sampling system 310, and may input the quantum-ready data to a quantum circuit that simulates molecular properties associated with the spectrum of smells. Furthermore, the olfaction system 320 may use a QAOA to generate, based on the quantum-ready data, a set of potential smells emitted by one or more objects contained in the sample, may use a spectrum matching technique to map the set of potential smells to a set of objects, and may generate a quantum graph that includes a number of vertices corresponding to a number of objects mapped to the set of potential smells. Furthermore, the olfaction system may use one or more quantum hybrid machine learning models to predict a future state of one or more detected smells.

In some implementations, the olfaction system 320 may include a user communication device and/or a user computing device. For example, the olfaction system 320 may include a wireless communication device, a mobile phone, a user equipment, a laptop computer, a tablet computer, a desktop computer, a wearable communication device (e.g., a smart wristwatch, a pair of smart eyeglasses, a head mounted display, or a virtual reality headset), or a similar type of device. Additionally, or alternatively, the olfaction system 320 may include a server communication device and/or a server computing device. For example, the olfaction system 320 may include an application server, a client server, a web server, a database server, a host server, a proxy server, a virtual server (e.g., executing on computing hardware), or a server in a cloud computing system. In some implementations, the olfaction system 320 includes computing hardware used in a cloud computing environment.

The network 330 includes one or more wired and/or wireless networks. For example, the network 330 may include a wireless wide area network (e.g., a cellular network or a public land mobile network), a local area network (e.g., a wired local area network or a wireless local area network (WLAN), such as a Wi-Fi network), a personal area network (e.g., a Bluetooth network), a near-field communication network, a telephone network, a private network, the Internet, and/or a combination of these or other types of networks. The network 330 enables communication among the devices of environment 300.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
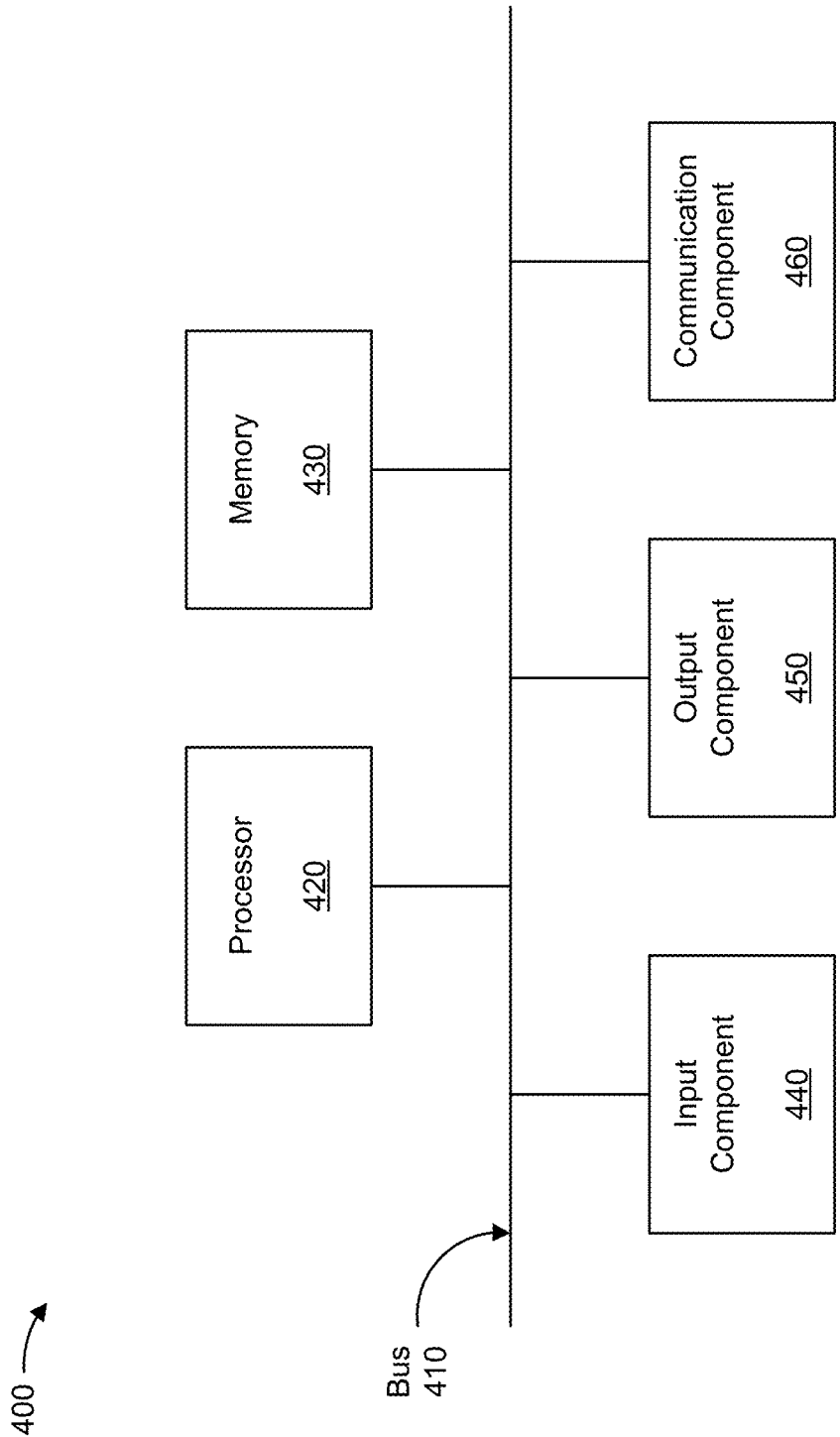
FIG. 4 is a diagram of example components of one or more devices of FIG. 2.

FIG. 4 is a diagram of example components of a device 400, which may correspond to sampling system 310, olfaction system 320, a sensor, and/or a sampling component as described herein. In some implementations, sampling system 310, olfaction system 320, the sensor, and/or sampling component include one or more devices 400 and/or one or more components of device 400. As shown in FIG. 4, device 400 may include a bus 410, a processor 420, a memory 430, an input component 440, an output component 450, and a communication component 460.

Bus 410 includes one or more components that enable wired and/or wireless communication among the components of device 400. Bus 410 may couple together two or more components of FIG. 4, such as via operative coupling, communicative coupling, electronic coupling, and/or electric coupling. Processor 420 includes a central processing unit, a graphics processing unit, a microprocessor, a controller, a microcontroller, a digital signal processor, a field-programmable gate array, an application-specific integrated circuit, and/or another type of processing component. Processor 420 is implemented in hardware, firmware, or a combination of hardware and software. In some implementations, processor 420 includes one or more processors capable of being programmed to perform one or more operations or processes described elsewhere herein.

Memory 430 includes volatile and/or nonvolatile memory. For example, memory 430 may include random access memory (RAM), read only memory (ROM), a hard disk drive, and/or another type of memory (e.g., a flash memory, a magnetic memory, and/or an optical memory). Memory 430 may include internal memory (e.g., RAM, ROM, or a hard disk drive) and/or removable memory (e.g., removable via a universal serial bus connection). Memory 430 may be a non-transitory computer-readable medium. Memory 430 stores information, instructions, and/or software (e.g., one or more software applications) related to the operation of device 400. In some implementations, memory 430 includes one or more memories that are coupled to one or more processors (e.g., processor 420), such as via bus 410.

Input component 440 enables device 400 to receive input, such as user input and/or sensed input. For example, input component 440 may include a touch screen, a keyboard, a keypad, a mouse, a button, a microphone, a switch, a sensor, a global positioning system sensor, an accelerometer, a gyroscope, and/or an actuator. Output component 450 enables device 400 to provide output, such as via a display, a speaker, and/or a light-emitting diode. Communication component 460 enables device 400 to communicate with other devices via a wired connection and/or a wireless connection. For example, communication component 460 may include a receiver, a transmitter, a transceiver, a modem, a network interface card, and/or an antenna.

Device 400 may perform one or more operations or processes described herein. For example, a non-transitory computer-readable medium (e.g., memory 430) may store a set of instructions (e.g., one or more instructions or code) for execution by processor 420. Processor 420 may execute the set of instructions to perform one or more operations or processes described herein. In some implementations, execution of the set of instructions, by one or more processors 420, causes the one or more processors 420 and/or the device 400 to perform one or more operations or processes described herein. In some implementations, hardwired circuitry is used instead of or in combination with the instructions to perform one or more operations or processes described herein. Additionally, or alternatively, processor 420 may be configured to perform one or more operations or processes described herein. Thus, implementations described herein are not limited to any specific combination of hardware circuitry and software.

The number and arrangement of components shown in FIG. 4 are provided as an example. Device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
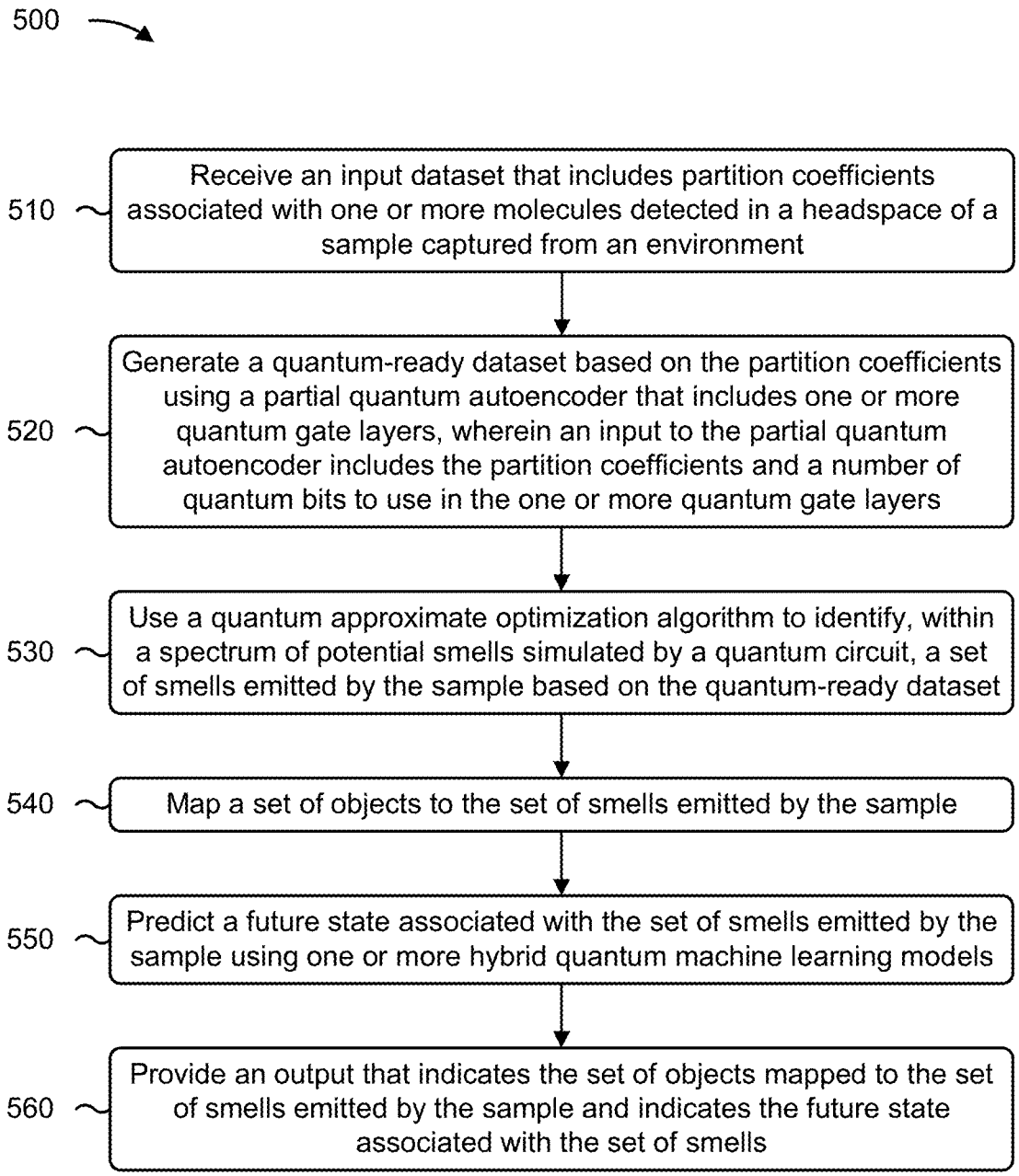
FIG. 5 is a flowchart of an example process associated with a virtual nose using quantum machine learning and quantum simulation, as described herein.

FIG. 5 is a flowchart of an example process 500 associated with a virtual nose that may perform machine olfaction using quantum machine learning and quantum simulation. In some implementations, one or more process blocks of FIG. 5 are performed by an olfaction system (e.g., olfaction system 320). In some implementations, one or more process blocks of FIG. 5 may be performed by another device or a group of devices separate from or including the olfaction system, such as a sampling system (e.g., sampling system 310). Additionally, or alternatively, one or more process blocks of FIG. 5 may be performed by one or more components of device 400, such as processor 420, memory 430, input component 440, output component 450, and/or communication component 460.

As shown in FIG. 5, process 500 may include receiving an input dataset that includes partition coefficients associated with one or more molecules detected in a headspace of a sample captured from an environment (block 510). For example, the olfaction system may receive an input dataset that includes partition coefficients associated with one or more molecules detected in a headspace of a sample captured from an environment, as described above.

As further shown in FIG. 5, process 500 may include generating a quantum-ready dataset based on the partition coefficients using a partial quantum autoencoder that includes one or more quantum gate layers, wherein an input to the partial quantum autoencoder includes the partition coefficients and a number of quantum bits to use in the one or more quantum gate layers (block 520). For example, the olfaction system may generate a quantum-ready dataset based on the partition coefficients using a partial quantum autoencoder that includes one or more quantum gate layers, wherein an input to the partial quantum autoencoder includes the partition coefficients and a number of quantum bits to use in the one or more quantum gate layers, as described above. In some implementations, an input to the partial quantum autoencoder includes the partition coefficients and a number of quantum bits to use in the one or more quantum gate layers.

As further shown in FIG. 5, process 500 may include using a quantum approximate optimization algorithm to identify, within a spectrum of potential smells simulated by a quantum circuit, a set of smells emitted by the sample based on the quantum-ready dataset (block 530). For example, the olfaction system may use a quantum approximate optimization algorithm to identify, within a spectrum of potential smells simulated by a quantum circuit, a set of smells emitted by the sample based on the quantum-ready dataset, as described above.

As further shown in FIG. 5, process 500 may include mapping a set of objects to the set of smells emitted by the sample (block 540). For example, the olfaction system may map a set of objects to the set of smells emitted by the sample, as described above.

As further shown in FIG. 5, process 500 may include predicting a future state associated with the set of smells emitted by the sample using one or more hybrid quantum machine learning models (block 550). For example, the olfaction system may predict a future state associated with the set of smells emitted by the sample using one or more hybrid quantum machine learning models, as described above.

As further shown in FIG. 5, process 500 may include providing an output that indicates the set of objects mapped to the set of smells emitted by the sample and indicates the future state associated with the set of smells (block 560). For example, the olfaction system may provide an output that indicates the set of objects mapped to the set of smells emitted by the sample and indicates the future state associated with the set of smells, as described above.

Process 500 may include additional implementations, such as any single implementation or any combination of implementations described below and/or in connection with one or more other processes described elsewhere herein.

In a first implementation, process 500 includes generating a quantum graph that includes a set of vertices to represent the set of objects that are mapped to the set of smells emitted by the sample and a set of edges connecting the set of vertices to represent conditions associated with the set of objects, and providing, to a sampling system, feedback to control a size of a next sample captured from the environment in a next olfaction iteration, wherein the feedback causes the sampling system to increase or decrease the size of the next sample based on a quantity of vertices in the quantum graph.

In a second implementation, alone or in combination with the first implementation, the one or more quantum gate layers in the partial quantum autoencoder include an initial quantum gate layer that creates a set of quantum states that add a superposition quality to the partition coefficients based on the number of quantum bits.

In a third implementation, alone or in combination with one or more of the first and second implementations, the one or more quantum gate layers in the partial quantum autoencoder include a second quantum gate layer that includes a set of quantum gates that parameterize the set of quantum states based on one or more tunable parameters.

In a fourth implementation, alone or in combination with one or more of the first through third implementations, the one or more quantum gate layers in the partial quantum autoencoder include a final quantum gate layer that removes one or more quantum states from the parameterized set of quantum states and outputs the quantum-ready dataset.

In a fifth implementation, alone or in combination with one or more of the first through fourth implementations, the quantum circuit simulates one or more of molecular vibrations or molecular bonds associated with the spectrum of potential smells.

In a sixth implementation, alone or in combination with one or more of the first through fifth implementations, the quantum circuit includes a sequence of alternating Hamiltonian cost layers and Hamiltonian mixer layers.

In a seventh implementation, alone or in combination with one or more of the first through sixth implementations, the future state associated with the set of smells includes one or more of a dispersion, a strength, or a duration of the set of smells over time.

In an eighth implementation, alone or in combination with one or more of the first through seventh implementations, the future state is predicted based on a set of parameters that include one or more of the partition coefficients associated with the one or more molecules, a wind direction in the environment, a wind speed in the environment, a humidity in the environment, or a temperature in the environment.

Although FIG. 5 shows example blocks of process 500, in some implementations, process 500 includes additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise forms disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   receiving, by a device, an input dataset that includes partition coefficients associated with one or more molecules detected in a headspace of a sample captured from an environment;
   generating, by the device, a quantum-ready dataset based on the partition coefficients using a partial quantum autoencoder that includes one or more quantum gate layers,
      wherein an input to the partial quantum autoencoder includes the partition coefficients and a number of quantum bits to use in the one or more quantum gate layers;
   using, by the device, a quantum approximate optimization algorithm to identify, within a spectrum of potential smells simulated by a quantum circuit that comprises a combination of alternating Hamiltonian cost layers and Hamiltonian mixer layers, based on interaction of molecular properties of different molecules, a set of smells emitted by the sample based on the quantum-ready dataset;
   mapping, by the device, a set of objects to the set of smells emitted by the sample;
   predicting, by the device, a future state associated with the set of smells emitted by the sample using one or more hybrid quantum machine learning models based on parameters within the environment; and
   providing, by the device, an output that indicates the set of objects mapped to the set of smells emitted by the sample and indicates the future state associated with the set of smells.

2. The method of claim 1, further comprising:
   generating a quantum graph that includes a set of vertices to represent the set of objects that are mapped to the set of smells emitted by the sample and a set of edges connecting the set of vertices to represent conditions associated with the set of objects; and
   providing, to a sampling system, feedback to control a size of a next sample captured from the environment in a next olfaction iteration,
      wherein the feedback causes the sampling system to increase or decrease the size of the next sample based on a quantity of vertices in the quantum graph.

3. The method of claim 1, wherein the one or more quantum gate layers in the partial quantum autoencoder include an initial quantum gate layer that creates a set of quantum states that add a superposition quality to the partition coefficients based on the number of quantum bits.

4. The method of claim 3, wherein the one or more quantum gate layers in the partial quantum autoencoder include a second quantum gate layer that includes a set of quantum gates that parameterize the set of quantum states based on one or more tunable parameters.

5. The method of claim 4, wherein the one or more quantum gate layers in the partial quantum autoencoder include a final quantum gate layer that removes one or more quantum states from the parameterized set of quantum states and outputs the quantum-ready dataset.

6. The method of claim 1, wherein the quantum circuit simulates one or more of molecular vibrations or molecular bonds associated with the spectrum of potential smells.

7. The method of claim 1, wherein the future state associated with the set of smells includes one or more of a dispersion, a strength, or a duration of the set of smells over time.

8. The method of claim 1, wherein the future state is predicted based on a set of parameters that include one or more of the partition coefficients associated with the one or more molecules, a wind direction in the environment, a wind speed in the environment, a humidity in the environment, or a temperature in the environment.

9. The method of claim 1, wherein the Hamiltonian cost layer is represented as $e^{-\alpha H_c}$ and the Hamiltonian mixer layer is represented as $e^{-\beta i H_m}$, and wherein initializing $\alpha$ and $\beta$ to optimize the quantum circuit such that the output by the quantum circuit based on the optimization indicates the set of objects to the set of smells that is identified based on the quantum-ready dataset.

10. A device, comprising:
one or more memories; and
one or more processors, coupled to the one or more memories, configured to:
receive an input dataset that includes partition coefficients associated with one or more molecules detected in a headspace of a sample captured from an environment;
generate a quantum-ready dataset based on the partition coefficients using a partial quantum autoencoder that includes one or more quantum gate layers,
wherein an input to the partial quantum autoencoder includes the partition coefficients and a number of quantum bits to use in the one or more quantum gate layers;
use a quantum approximate optimization algorithm to identify, within a spectrum of potential smells simulated by a quantum circuit that comprises a combination of alternating Hamiltonian cost layers and Hamiltonian mixer layers, based on interaction of molecular properties of different molecules, a set of smells emitted by the sample based on the quantum-ready dataset;
map a set of objects to the set of smells emitted by the sample;
provide an output that indicates the set of objects mapped to the set of smells emitted by the sample; and
provide, to a sampling system, feedback to control a size of a next sample captured from the environment in a next olfaction iteration based on a quantity of objects in the set of objects mapped to the set of smells emitted by the sample.

11. The device of claim 10, wherein the one or more quantum gate layers in the partial quantum autoencoder include an initial quantum gate layer that creates a set of quantum states that add a superposition quality to the partition coefficients based on the number of quantum bits.

12. The device of claim 11, wherein the one or more quantum gate layers in the partial quantum autoencoder include a second quantum gate layer that includes a set of quantum gates that parameterize the set of quantum states based on one or more tunable parameters.

13. The device of claim 12, wherein the one or more quantum gate layers in the partial quantum autoencoder include a final quantum gate layer that removes one or more quantum states from the parameterized set of quantum states and outputs the quantum-ready dataset.

14. The device of claim 10, wherein the one or more processors are further configured to:
predict a future state associated with the set of smells emitted by the sample using one or more hybrid quantum machine learning models,
wherein the output indicates the future state associated with the set of smells.

15. The device of claim 14, wherein the future state associated with the set of smells includes one or more of a dispersion, a strength, or a duration of the set of smells over time.

16. The device of claim 14, wherein the one or more hybrid quantum machine learning models include one or more of a quantum regression model or a quantum neural network based on a survival analysis algorithm.

17. A non-transitory computer-readable medium storing a set of instructions, the set of instructions comprising:
one or more instructions that, when executed by one or more processors of a device, cause the device to:
receive an input dataset that includes partition coefficients associated with one or more molecules detected in a headspace of a sample captured from an environment;
generate a quantum-ready dataset based on the partition coefficients;
use a quantum approximate optimization algorithm to identify, within a spectrum of potential smells simulated by a quantum circuit that comprises a combination of alternating Hamiltonian cost layers and Hamiltonian mixer layers, based on interaction of molecular properties of different molecules, a set of smells emitted by the sample based on the quantum-ready dataset;
perform spectrum matching to map the set of smells to a set of objects;
predict a future state associated with the set of smells emitted by the sample using one or more machine learning models based on parameters within the environment; and
provide an output that indicates the set of objects mapped to the set of smells emitted by the sample and indicates the future state associated with the set of smells.

18. The non-transitory computer-readable medium of claim 17, wherein the one or more instructions further cause the device to:
provide, to a sampling system, feedback to control a size of a next sample captured from the environment in a next olfaction iteration based on the predicted future state associated with the set of smells.

19. The non-transitory computer-readable medium of claim 17, wherein the quantum-ready dataset is generated using a partial quantum autoencoder.

20. The non-transitory computer-readable medium of claim 17, wherein the quantum circuit simulates molecular properties associated with the spectrum of potential smells.

* * * * *